United States Patent [19]
Scharlemann

[11] Patent Number: 6,105,408
[45] Date of Patent: Aug. 22, 2000

[54] NON-DESTRUCTIVE TESTING OF STEEL DURING ROLLING

[75] Inventor: Horst Scharlemann, Hagen, Germany

[73] Assignee: Georgsmarienhütte GmbH, Georgsmarienhütte, Germany

[21] Appl. No.: 09/335,667

[22] Filed: Jun. 18, 1999

[30] Foreign Application Priority Data

Jul. 24, 1998 [DE] Germany .......................... 198 33 386
Apr. 3, 1999 [DE] Germany .......................... 199 15 203

[51] Int. Cl.$^7$ .................................................. B21B 38/00
[52] U.S. Cl. ........................................... 72/31.07; 72/11.2
[58] Field of Search ................................ 72/8.1, 8.3–8.9,
72/11.1, 11.2–11.6, 12.7, 31.02, 31.03,
31.04, 31.06, 31.07, 365.2; 73/587, 637,
638

[56] References Cited

U.S. PATENT DOCUMENTS

| | | | |
|---|---|---|---|
| 4,538,463 | 9/1985 | Pease | 72/17.3 |
| 4,918,989 | 4/1990 | Desruelles et al. | 73/627 |
| 4,927,299 | 5/1990 | Ramalingam et al. | 72/20.1 |
| 5,048,340 | 9/1991 | Thompson et al. | 73/597 |
| 5,163,013 | 11/1992 | Herzer et al. | 364/563 |
| 5,635,780 | 6/1997 | Kohlert et al. | 310/68 R |
| 5,721,379 | 2/1998 | Palmer et al. | 75/643 |

FOREIGN PATENT DOCUMENTS 3204797   12/1983   Germany .

*Primary Examiner*—Ed Tolan
*Attorney, Agent, or Firm*—Collard & Roe, P.C.

[57] ABSTRACT

In the non-destructive testing of still readily deformable steel for interior flaws by ultrasound waves emitted by an ultrasound probe at a roll used for rolling the steel, the ultrasound waves are passed through the roll serving as forward run for the ultrasound waves before they impinge upon the steel to be tested and the ultrasound waves are so oriented that they impinge on the surface of the steel at a point where the steel has the closest contact with the roll and where the maximum slap-back occurs.

21 Claims, 3 Drawing Sheets

NON-DESTRUCTIVE TESTING OF STEEL DURING ROLLING

BACKGROUND OF THE INVENTION

1. Field of the Invention

The present invention relates to a method and an apparatus for the non-destructive testing for interior flaws of still well deformable steel by ultrasound waves emitted by an ultrasound probe at a roll used for rolling the steel.

2. Description of the Prior Art

Non-destructive testing by ultrasound has been known for a long time.

German patent No. 3,204,797, for example, describes a method in which a finished work piece, such as a pipe, is subjected to ultrasound waves, the ultrasound energy being transmitted from the probe to the work piece along a path passing through an aqueous coupling medium.

The detection of interior flaws in the work piece is accomplished in the so-called impulse-echo method, that is, the ultrasound waves emitted from the probe are reflected, on the one hand, from the surface and, on the other hand, from the back wall of the work piece after the waves have passed therethough. This produces two more or less sharp impulses with a certain amplitude in the test indicator. If the ultrasound wave impinges on a flaw in the work piece, such as a crack, an occlusion, etc., it is also reflected at this location, causing a third impulse, i.e. a flaw impulse, to be generated. Since the ultrasound energy passes back and forth several times between the location of the flaw and the probe, the cited German patent proposes a method for masking such additional impulses, which are of no interest, for instance impulses which result from possible impurities in the coupling medium. The test takes place on the finished work piece by the use of a liquid coupling medium which may contain foreign bodies which may disturb the testing.

SUMMARY OF THE INVENTION

It is a primary object of this invention to provide a method for continuously finding interior flaws in steel while it is being rolled, i.e. while the steel to be tested is hot and still deformable, which means that the use of a liquid coupling medium, such as water, may not be feasible.

In the continuous casting of steel, for example in the shape of rods, the hot, readily deformable ingot leaves the mold and begins to solidify as it passes along an arcuate path into the horizontal. Gravity forces cause any foreign bodies in the liquid steel to be concentrated more between the ingot axis and the already solidified interior of the ingot. The invention is concerned primarily with detecting such flaws during the rolling process.

The above and other objects are accomplished according to one aspect of the invention with a method for the non-destructive testing for interior flaws of still readily deformable steel by ultrasound waves emitted by an ultrasound probe at a roll used for rolling the steel, which comprises the step of passing the ultrasound waves through the roll serving as forward run for the ultrasound waves, preferably close to the circumference thereof, before they impinge upon the steel to be tested and orienting the ultrasound waves so that they impinge on the surface thereof at a point where the steel has the closest contact with the roll and where the maximum slap-back occurs.

In this method, the test and rolling locations coincide so that a rapid reaction is possible if significant flaws are detected.

It is desired to impinge the ultrasound waves on the surface of the steel to be tested where intensive deformation in a radial direction is still effected, i.e. where the steel ingot enters the roll stand. Experiments have shown that a maximum slap-back, i.e. an echo from the back wall, is obtained if the steel is not subjected to any tensile forces, which means that a proper synchronization between the succeeding roll stands must be assured.

Since the slap-back is an indicium for the good synchronization of the succeeding roll stands, the method of the present invention also makes it possible to produce such a synchronization by optimizing the slap-back.

It is another advantage of this invention that the roll itself serves as the forward run of the ultrasound waves and as a coupling path of the ultrasound waves, and spontaneously changing flaw locations in a liquid coupling medium are avoided. Furthermore, the steel is particularly fine-grained and fault-free, especially close to the circumference of the ingot.

The first reflection of the ultrasound waves takes place at the interface between the relatively cold roll and the hot steel being rolled, and the non-reflected component is refracted because its propagation velocity differs from that of the impinging waves, passes through the steel being tested and is reflected from the opposite interface. If there are flaw locations, such as occlusions, between the first reflection and the slap-back at the opposite interface, that is, the back wall of the steel ingot, the ultrasound waves are also reflected by such flaws, which generates in the receiver of the probe an impulse of a certain amplitude which lies in the amplitude-time diagram between the two other impulses.

Preferably, the ultrasound waves are so oriented that they are reflected back to the receiver of the ultrasound probe after they have penetrated the steel to be tested. In this way, the steel is fully tested throughout its thickness. Any type of ultrasound probe may be used.

Flaws close to the circumference of the steel ingot may be readily detected if the ultrasound waves are so oriented towards the surface of the steel to be tested that they are reflected several times in the steel close to the surface and along the circumference thereof before they are reflected back to the receiver of the ultrasound probe. The ultrasound emitter and receiver are separately arranged in the probe, and the ultrasound probe may emit longitudinal or transverse ultrasound waves.

According to another aspect of the invention, there is provided an apparatus for the non-destructive testing for interior flaws of still readily deformable steel, which comprises an ultrasound probe emitting ultrasound waves so arranged at a roll used for rolling the steel that the roll serves as forward run of the ultrasound waves and the ultrasound waves pass through the roll, preferably close to the circumference thereof, before they impinge upon the steel to be tested, and that the probe is so oriented that the ultrasound waves impinge on the surface thereof at a point where the steel has the closest contact with the roll.

In one preferred embodiment, the apparatus comprises a multi-roll stand for rolling the steel in a gap defined by a plurality of rolls surrounding the gap, the rolls being disc-shaped, and at least one ultrasound probe is arranged at each roll. The apparatus operates in a most accurate and effective manner if at least one ultrasound probe is arranged at each side of each disc-shaped roll.

The ultrasound probe may be arranged in an annular groove of wedge-shaped cross section milled into a side of the roll, or on an annular shoulder of wedge-shaped cross section projecting from a side of the roll. While the steel is rolled, the surface of the groove or shoulder pointing to the circumference of the roll moves below the detector face of the stationary probe and, if desired, a water film may fill a gap between the ultrasound probe and the roll.

In another preferred embodiment, the apparatus comprises two profiled rolls for rolling the steel in a gap defined by walls of the rolls, and the ultrasound probe is arranged laterally of the gap so that the ultrasound waves are oriented perpendicularly to a respective gap wall. Preferably, a respective ultrasound probe is arranged laterally of opposite gap walls in neighboring gaps defined by walls of the roll, and the ultrasound probes pass ultrasound waves through the steel separating the neighboring gaps and serving as a forward run for the waves. Preferably, the two probes are oriented to emit diametrically opposed ultrasound waves. This arrangement is particularly useful for profiled rolls with rectangular gaps.

If the profiled rolls define gaps of diamond-shaped cross section for rolling the steel, the probes may be positioned at the outer circumference of the rolls so that the ultrasound waves penetrate the entire rolls before they enter the gap and impinge upon the steel therein. Several probes may be used to send sound waves through the steel from different sides.

Especially useful in the practice of this invention are ultrasound probes which comprise piezoelectric vibration generators for generating the ultrasound waves.

The direction of the ultrasound waves may be adjusted according to one feature of the present invention with ultrasound probes comprising a plurality of independently controllable piezoelectric vibration generators for generating an ultrasound wave front. The piezoelectric vibration generators are actuated in a timed sequence. Dependent on the difference in time, an ultrasound wave front with different directions of propagation of the wave front results.

The direction of the ultrasound waves may also be obtained by arranging the ultrasound probe displaceably, for example tiltably, in, or perpendicularly to, the rolling direction.

The ultrasound probe may be coupled to the roll at a curved plane, which may be either convex or concave. This enables the ultrasound waves to be focussed or defocussed.

Preferably, the rolls with the probes are part of a roll stand preceding a finishing roll stand. In this case, the steel is still readily deformable. Importantly, the rolling mill needs to be adjusted only once so that mounting and adjusting are reduced to a minimum.

The apparatus works with longitudinal as well as transverse ultrasound waves. This has the particular advantage that radial flaws close to the edge may be detected by transverse as well as longitudinal waves by suitably selecting the impinging angles of the waves.

BRIEF DESCRIPTION OF THE DRAWING

The above and other objects, advantages and features of the invention will become more apparent from the following detailed description of certain now preferred embodiments thereof, taken in conjunction with the accompanying schematic drawing wherein.

DETAILED DESCRIPTION OF THE PREFERRED EMBODIMENTS

Figure 1:
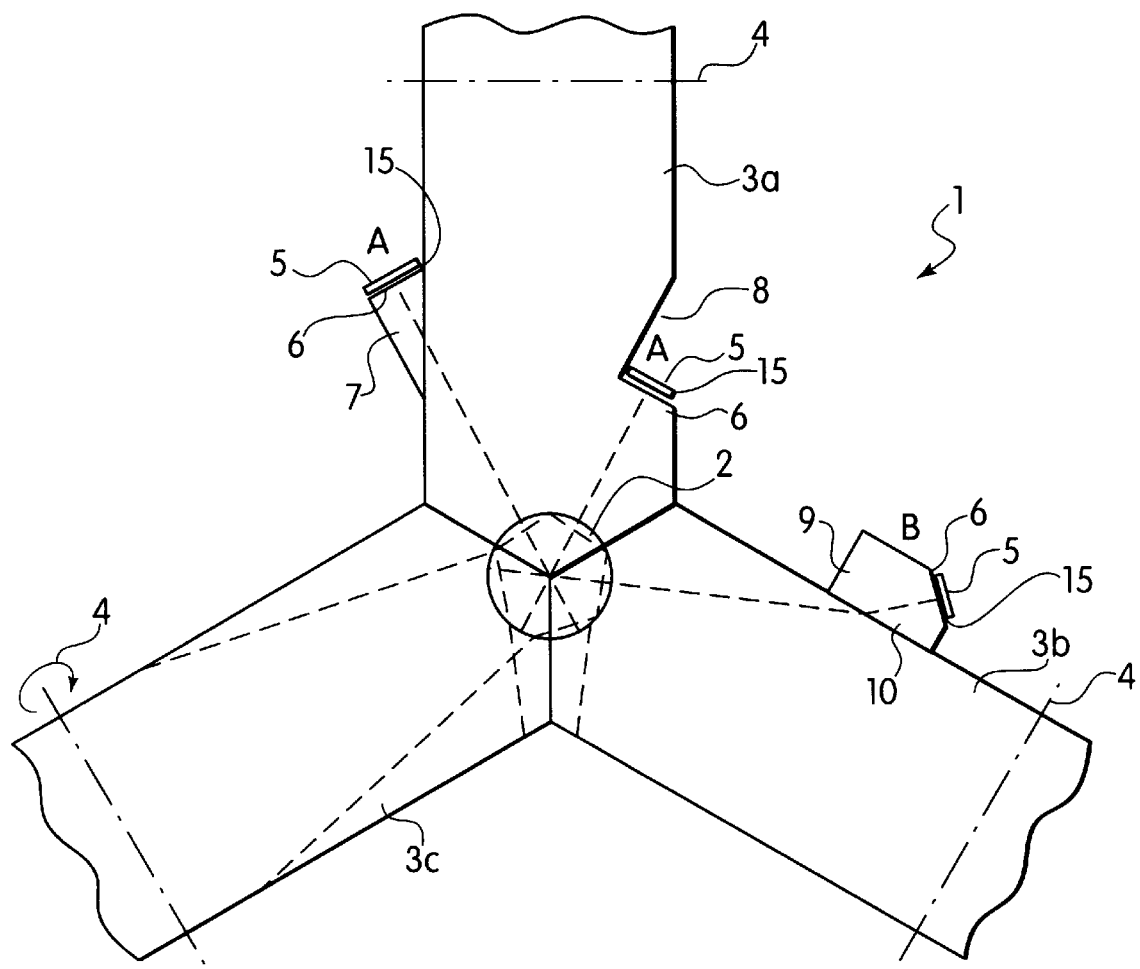
FIG. 1 is a fragmentary view of a multi-roll stand with three disc-shaped rolls and showing three alternative arrangements of ultrasound probes at the rolls.

Referring now to the drawing and first to FIG. 1, there is shown stand 1 with three disc-shaped rolls 3a, 3b, 3c which are arranged in star formation around gap 2 of circular cross section for rolling a round steel rod. The disc-shaped rolls rotate about axes of rotation 4.

FIG. 1 illustrates three embodiments of an apparatus for the non-destructive testing for interior flows of still readily deformable steel to be rolled in gap 2. In each embodiment, ultrasound probe 5 emitting ultrasound waves is so arranged at roll 3a, 3b, 3c that the roll serves as forward run of the ultrasound waves and the ultrasound waves pass through the roll before they impinge upon the steel in gap 2, and probe 5 is so oriented that the ultrasound waves impinge on the surface of the steel at a point where the steel has the closest contact with the roll.

As shown by the broken lines in FIG. 1, ultrasound probes 5 are so arranged that the ultrasound waves pass through rolls 3a, 3b, 3c close to the circumference thereof. The illustrated apparatus comprises a multi-roll stand, the rolls are disc-shaped, and at least one ultrasound probe 5 is arranged at each roll.

At roll 3a, two alternative arrangements of schematically illustrated probes 5 are shown. At the right side of roll 3a, probe 5 is arranged in annular groove 8 of wedge-shaped cross section, which is milled into the side of the disc-shaped roll and forms coupling surface 6 for the probe. At the left side, the probe is arranged on coupling surface 6 of annular shoulder 7 projecting from a side of roll 3a.

Coupling surfaces 6 are so oriented that the longitudinal ultrasound waves generated by probes 5, and received thereby upon reflection, impinge perpendicularly upon the steel being rolled in gap 2 after the waves in a forward run have passed through roll 3a close to the circumference thereof.

As merely schematically indicated at roll 3c, an ultrasound probe at the roll may also be so oriented that the ultrasound waves are propagated in a direction that differs from a perpendicular impingement on the surface of the steel being rolled. In this case, as shown in broken lines, the ultrasound waves pass through the steel at the interface with the rolls near the circumference of the rolled steel while being reflected several times.

In the embodiment illustrated at roll 3b, annular shoulder 9 of trapezoid cross section is mounted on the roll and an inclined plane of shoulder 9 forms coupling surface 6 for probe 5. The probe is so oriented that it emits transverse ultrasound waves which are refracted at interface 10 between shoulder 9 and roll 3b so that they also impinge perpendicularly on the steel in gap 2.

If desired, each roll 3a, 3b, 3c may have ultrasound probes of any one of the illustrated embodiments at each side of the disc-shaped roll.

Figure 2:
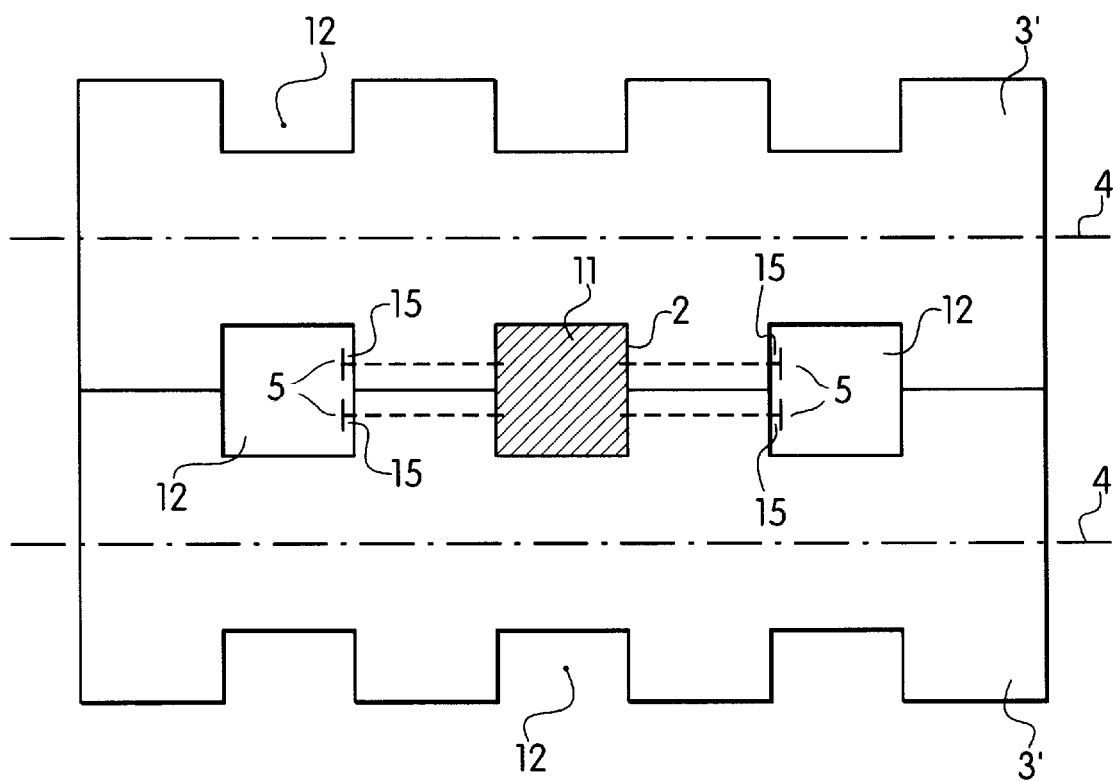
FIG. 2 is a side view of two profiled rolls defining a rectangular gap for rolling flat-ended steel ingots.

The embodiment illustrated in FIG. 2 comprises two profiled rolls 3' for rolling steel 11 in gap 2 defined by walls of grooves in the rolls, and ultrasound probes 5 are arranged laterally of gap 2 in further grooves 12 so that the ultrasound waves are oriented perpendicularly to a respective one of the walls of gap 2. The probes are oriented to emit diametrically opposed ultrasound waves passing horizontally through the steel. In the illustrated embodiment, a flat-sided, rectangular steel ingot is produced.

Figure 3:
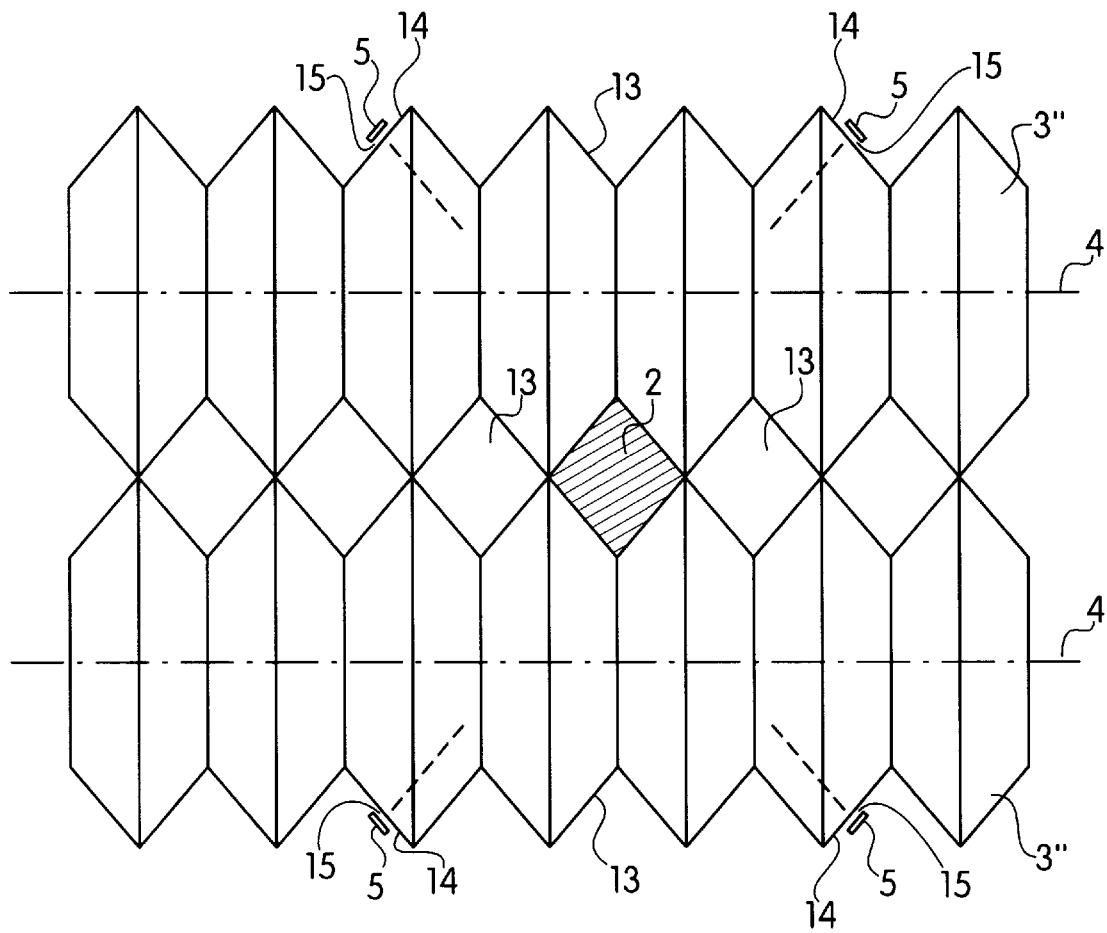
FIG. 3 is a like view of two profiled rolls for rolling steel ingots of diamond-shaped cross section.

FIG. 3 also illustrates a two-roll stand but, in this case, rolls 3" are so profiled that they form a gap 2 of diamond-shaped cross section. For this purpose, the grooves 13 in the profiled rolls are of triangular cross section so that complementary grooves in the two rolls form the diamond-shaped gaps. Ultrasound probes 5 are at a side of rolls 3" opposite the side defining gap 2 so that the ultrasound waves emitted by the probes pass through the rolls before they impinge perpendicularly upon the steel being rolled in gap 2. As shown, probes 5 are preferably positioned at opposite sides of gap 2 on coupling surfaces 14 formed by the flanks of the grooves in the rolls.

In all instances, ultrasound probes 5 are arranged stationary and the rolls with their coupling surfaces move by the probes as they rotate about axes 4. As shown, a water film 15 may be provided between ultrasound probe and the roll at which it is arranged.

The ultrasound waves preferably impinge upon the steel at a location immediately behind where the extruded steel enters the gap between the rolls, i.e. at a point where the roll and the steel surface is in the closest contact. Advantageously, the rolls at which the ultrasound probes 5 are arranged are part of a roll stand preceding a finishing roll stand.

Usefully, the ultrasound probe comprises a piezoelectric vibration generator for generating the ultrasound waves, and it may comprise a plurality of independently controllable piezoelectric vibration generators for generating an ultrasound wave front. Also, the ultrasound probes may be displaceable, for instance tiltable, in the rolling direction or in a direction perpendicular to the rolling direction. Furthermore, the ultrasound probe may be coupled to the roll at a concavely or convexly curved plane.

In operation, the illustrated apparatus provides a method for the non-destructive testing for interior flaws of still readily deformable steel by ultrasound waves emitted by ultrasound probes 5 at a roll 3a, 3b, 3c, 3', 3" used for rolling the steel, in which the ultrasound waves are passed through the roll serving as forward run for the ultrasound waves before they impinge upon the steel to be tested, and the ultrasound waves are so oriented that they impinge on the surface thereof at a point where the steel has the closest contact with the roll and where the maximum slap-back occurs.

What is claimed is:

1. A method for the non-destructive testing of still readily deformable steel for interior flaws by ultrasound waves emitted by an ultrasound probe at a roll used for rolling the steel, which comprises the step of passing the ultrasound waves through the roll serving as forward run for the ultrasound waves before they impinge upon the steel to be tested and orienting the ultrasound waves so that they impinge on the surface thereof at a point where the steel has the closest contact with the roll and where the maximum slap-back occurs, and wherein the waves reflect off the interior flaws of the steel and are received and evaluated by the ultrasound probe to pinpoint the location of the interior flaws.

2. The method of claim 1, wherein the ultrasound waves are passed through the roll close to the circumference thereof.

3. The method of claim 1, wherein the ultrasound waves are so oriented that they are reflected back to the ultrasound probe after they have penetrated the steel to be tested.

4. The method of claim 1, wherein the ultrasound waves are so oriented towards the surface of the steel to be tested that they are reflected several times in the steel close to the surface and along the circumference thereof before they are reflected back to the ultrasound probe.

5. The method of claim 1, wherein the ultrasound probe emits longitudinal ultrasound waves.

6. The method of claim 1, wherein the ultrasound probe emits transverse ultrasound waves.

7. An apparatus for the non-destructive testing of still readily deformable steel for interior flaws, comprising an ultrasound probe emitting ultrasound waves so arranged at a roll used for rolling the steel that the roll serves as forward run of the ultrasound waves and the ultrasound waves pass through the roll before they impinge upon the steel to be tested, and that the probe is so oriented that the ultrasound waves impinge on the surface thereof at a point where the steel has the closest contact with the roll, and wherein the waves reflect off the interior flaws of the steel and are received and evaluated by the ultrasound probe to pinpoint the location of the interior flaws.

8. The apparatus of claim 7, wherein the ultrasound probe is so arranged that the ultrasound waves pass through the roll close to the circumference thereof.

9. The apparatus of claim 7, comprising a multi-roll stand for rolling the steel in a gap defined by a plurality of said rolls surrounding the gap, the rolls being disc-shaped, and at least one of said ultrasound probes being arranged at each one of said rolls.

10. The apparatus of claim 9, wherein at least one of said ultrasound probes is arranged at each side of each of said disc-shaped rolls.

11. The apparatus of claim 7, wherein the ultrasound probe is arranged in an annular groove in a side of the roll.

12. The apparatus of claim 7, wherein the ultrasound probe is arranged on an annular shoulder projecting from a side of the roll.

13. The apparatus of claim 7, comprising two profiled rolls for rolling the steel in a gap defined by walls of the rolls, and the ultrasound probe is arranged laterally of the gap so that the ultrasound waves are oriented perpendicularly to a respective one of the gap walls.

14. The apparatus of claim 13, wherein a respective one of said ultrasound probes is arranged laterally of opposite gap walls, and the ultrasound probes are oriented to emit diametrically opposed ultrasound waves.

15. The apparatus of claim 7, wherein the ultrasound probe comprises a piezoelectric vibration generator for generating the ultrasound waves.

16. The apparatus of claim 7, wherein the ultrasound probe comprises a plurality of independently controllable piezoelectric vibration generators for generating an ultrasound wave front.

17. The apparatus of claim 7, wherein the ultrasound probe is displaceable in the rolling direction.

18. The apparatus of claim 7, wherein the ultrasound probe is displaceable perpendicularly to the rolling direction.

19. The apparatus of claim 7, wherein the ultrasound probe is coupled to the roll at a curved plane.

20. The apparatus of claim 7, wherein the roll is part of a roll stand preceding a finishing roll stand.

21. The apparatus of claim 7, comprising a water film between ultrasound testing head and the roll.

* * * * *